US012060554B2

(12) United States Patent
Sabot et al.

(10) Patent No.: US 12,060,554 B2
(45) Date of Patent: Aug. 13, 2024

(54) METHOD FOR SELECTING AND AMPLIFYING POLYNUCLEOTIDES

(71) Applicant: Illumina, Inc., San Diego, CA (US)

(72) Inventors: Andrea Sabot, Nr Saffron Walden (GB); Roberto Rigatti, Nr Saffron Walden (GB); Min-Jui Richard Shen, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 211 days.

(21) Appl. No.: 17/470,284

(22) Filed: Sep. 9, 2021

(65) Prior Publication Data

US 2022/0064632 A1    Mar. 3, 2022

Related U.S. Application Data

(63) Continuation of application No. 16/786,198, filed on Feb. 10, 2020, now Pat. No. 11,142,759, which is a continuation of application No. 15/489,549, filed on Apr. 17, 2017, now Pat. No. 10,597,653, which is a continuation of application No. 14/611,991, filed on Feb. 2, 2015, now Pat. No. 9,624,489, which is a continuation of application No. 13/387,078, filed as application No. PCT/US2009/054945 on Aug. 25, 2009, now Pat. No. 8,999,642, which is a continuation-in-part of application No. 12/395,299, filed on Feb. 27, 2009, now abandoned.

(60) Provisional application No. 61/035,254, filed on Mar. 10, 2008.

(51) Int. Cl.
*C12N 15/10* (2006.01)
*C12Q 1/6806* (2018.01)
*C12Q 1/6837* (2018.01)
*C12Q 1/6874* (2018.01)

(52) U.S. Cl.
CPC ....... *C12N 15/1068* (2013.01); *C12Q 1/6806* (2013.01); *C12Q 1/6837* (2013.01); *C12Q 1/6874* (2013.01)

(58) Field of Classification Search
CPC .................................................. C12N 15/1068
See application file for complete search history.

(56) References Cited

U.S. PATENT DOCUMENTS

| 5,118,604 A | 6/1992 | Weissman |
| 5,302,509 A | 4/1994 | Cheeseman |
| 5,547,839 A | 8/1996 | Dower |
| 5,616,478 A | 4/1997 | Chetverin |
| 5,629,158 A | 5/1997 | Uhlen |
| 5,641,658 A | 6/1997 | Adams |
| 5,800,992 A | 9/1998 | Fodor |
| 5,837,466 A | 11/1998 | Lane |
| 5,922,574 A | 7/1999 | Minter |
| 5,935,788 A | 8/1999 | Burmer |
| 5,976,802 A | 11/1999 | Ansorge |
| 6,060,288 A | 5/2000 | Adams |
| 6,090,592 A | 7/2000 | Adams |
| 6,107,023 A | 8/2000 | Reyes |
| 6,251,610 B1 | 6/2001 | Gupte |
| 6,322,971 B1 | 11/2001 | Chetverin |
| 6,326,489 B1 | 12/2001 | Church |
| 6,361,947 B1 | 3/2002 | Dong |
| 6,511,803 B1 | 1/2003 | Church |
| 7,115,400 B1 | 10/2006 | Adessi |
| 8,728,764 B2 | 5/2014 | Boutell |
| 2002/0055100 A1 | 5/2002 | Kawashima |
| 2002/0061532 A1 | 5/2002 | Adams |
| 2002/0098499 A1 | 7/2002 | Asp |
| 2002/0127569 A1 | 9/2002 | Weisburg |
| 2003/0022207 A1 | 1/2003 | Balasubramanian |
| 2003/0055233 A1 | 3/2003 | Krull |
| 2003/0082576 A1 | 5/2003 | Jones |

(Continued)

FOREIGN PATENT DOCUMENTS

| DE | 10051564 | 8/2002 |
| EP | 0224126 | 6/1987 |

(Continued)

OTHER PUBLICATIONS

Illumina, "Optimizing Cluster Density on Illumina Sequencing Systems", pp. 1-12 (Year: 2016).*
Armougom, et al., Exploring Microbial Diversity Using 16S rRNA High-Throughput Methods, J. Compt. Sci. Systems Biol., 2:94-92 (2009).
Gasc, et al., Sequence capture by hybridization to explore modern and ancient genomic diversity in model and nonmodel organisms, Nucleic Acids Research, 44(10):4504-4518 (2016).
Holt, et al, The new paradigm of flow cell sequencing, Genome Research, 18(6):839-846 (2008).
13180255.5, Extended European Search Report mailed Nov. 6, 2013, 8 pages.

(Continued)

*Primary Examiner* — Gary Benzion
*Assistant Examiner* — Olayinka A Oyeyemi
(74) *Attorney, Agent, or Firm* — Knobbe Martens Olson & Bear LLP

(57) ABSTRACT

The invention provides methods for controlling the density of different molecular species on the surface of a solid support. A first mixture of different molecular species is attached to a solid support under conditions to attach each species at a desired density, thereby producing a derivatized support having attached capture molecules. The derivatized support is treated with a second mixture of different molecular species, wherein different molecular species in the second mixture bind specifically to the different capture molecules attached to the solid support. One or more of the capture molecules can be reversibly modified such that the capture molecules have a different activity before and after the second mixture of molecular species are attached. In particular embodiments, the different molecular species are nucleic acids that are reversibly modified to have different activity in an amplification reaction.

23 Claims, 8 Drawing Sheets
Specification includes a Sequence Listing.

(56) References Cited

U.S. PATENT DOCUMENTS

| | | |
|---|---|---|
| 2003/0108867 A1 | 6/2003 | Chee |
| 2004/0002090 A1 | 1/2004 | Mayer |
| 2004/0096853 A1 | 5/2004 | Mayer |
| 2004/0126765 A1 | 7/2004 | Adams |
| 2005/0100900 A1 | 5/2005 | Kawashima |
| 2005/0136441 A1 | 6/2005 | Carrino |
| 2006/0024681 A1 | 2/2006 | Smith |
| 2006/0134633 A1 | 6/2006 | Chen |
| 2006/0275782 A1 | 12/2006 | Gunderson |
| 2006/0292611 A1 | 12/2006 | Berka |
| 2007/0003924 A1 | 1/2007 | Yu |
| 2007/0128624 A1 | 6/2007 | Gormley |
| 2007/0269817 A1 | 11/2007 | Shapero |
| 2008/0009420 A1 | 1/2008 | Schroth |
| 2008/0242555 A1 | 10/2008 | Shen |
| 2009/0088327 A1 | 4/2009 | Rigatti |
| 2009/0093378 A1 | 4/2009 | Bignell |
| 2012/0157322 A1 | 6/2012 | Myllykangas |
| 2015/0050657 A1 | 2/2015 | Rigatti |
| 2020/0239875 A1 | 7/2020 | Sabot |

FOREIGN PATENT DOCUMENTS

| | | |
|---|---|---|
| EP | 0356021 | 2/1990 |
| EP | 0374665 | 6/1990 |
| EP | 0438292 | 7/1991 |
| EP | 0201184 | 12/1992 |
| EP | 0534858 | 3/1993 |
| EP | 0665293 | 8/1995 |
| EP | 0763135 | 3/1997 |
| EP | 1256632 | 11/2002 |
| EP | 1591541 | 11/2005 |
| EP | 1647602 | 4/2006 |
| EP | 2055788 | 5/2009 |
| GB | 0205153.0 | 4/2002 |
| GB | 2412170 | 9/2005 |
| GB | 0522310.2 | 12/2005 |
| WO | WO89/01050 | 2/1989 |
| WO | WO 89/09282 | 10/1989 |
| WO | WO 92/10587 | 6/1992 |
| WO | WO 1993/04199 | 3/1993 |
| WO | WO 94/02634 | 2/1994 |
| WO | WO 95/33073 | 12/1995 |
| WO | WO 96/04404 | 2/1996 |
| WO | WO 1996/032504 | 10/1996 |
| WO | WO 98/36094 | 8/1998 |
| WO | WO 98/44151 | 10/1998 |
| WO | WO 98/44152 | 10/1998 |
| WO | WO 00/18957 | 4/2000 |
| WO | WO 00/75374 | 12/2000 |
| WO | WO 01/49882 | 7/2001 |
| WO | WO 01/79553 | 10/2001 |
| WO | WO02/46456 | 6/2002 |
| WO | WO03/056030 | 7/2003 |
| WO | WO03/074734 | 9/2003 |
| WO | WO 03/102233 | 12/2003 |
| WO | WO2004/070005 | 8/2004 |
| WO | WO2004/072294 | 8/2004 |
| WO | WO2005/003375 | 1/2005 |
| WO | WO2005/040425 | 5/2005 |
| WO | WO2005/042781 | 5/2005 |
| WO | WO2005/068656 | 7/2005 |
| WO | WO2005/093094 | 10/2005 |
| WO | WO2006/110855 | 10/2006 |
| WO | WO2006/135342 | 12/2006 |
| WO | WO2007/010251 | 1/2007 |
| WO | WO2007/010252 | 1/2007 |
| WO | WO2007/010263 | 1/2007 |
| WO | WO2007/052006 | 5/2007 |
| WO | WO2007/076726 | 7/2007 |
| WO | WO2007/091077 | 8/2007 |
| WO | WO2007/107710 | 9/2007 |
| WO | WO2007/111937 | 10/2007 |
| WO | WO2008/002502 | 1/2008 |
| WO | WO 2009/004335 | 1/2009 |

OTHER PUBLICATIONS

U.S. Appl. No. 14/611,911 Notice of Allowance mailed Dec. 5, 2016, 8 pages.

Adessi, et al., "Solid Phase DNA amplification: characterisation of primer attachment and amplification mechanisms", Nucleic Acids Research 28, Jan. 8, 2000.

Bennett, et al., "Toward the $1000 Human Genome", Pharmacogenomics, Ashley Productions GB vol. 6 No 4, 2005 373-382.

Bentley, et al., "Accurate whole human genome sequencing using reversible terminator chemistry", Nature, vol. 156, 2008, 53-59.

Braslavsky, et al., "Sequence information can be obtained from single DNA molecules", PNAS, 100(7), Apr. 1, 2003, 3960-3964.

Cheng, et al., "Chip PCR II Investigation of different PCR ampification systems in microfabricaled silicon-glass chips", Nucleic Acids Research 24, 1996, 380-385.

Dubiley, et al., "Polymorphism analysis and gene detection by minisequencing on an array of gel-immobilized primers", Nucleic Acids Research 27, Jan. 6, 1999.

Fu, et al., "Sequencing Double-stranded DNA by Strand Displacement", Nucleic Acids Research vol. 25 No. 3, 1997, 577-679.

Gnirke, et al., "Solution hybrid selection with ultra-long oligonucleolides for massively parallel targeted sequencing", Nature Biotechnology, Nature Publishing Group, New York, NY, US, vol. 27, No. 2, Feb. 1, 2009, 182-189, XP002658414.

Helfman, et al., "Identification of clones that encode chicken tropomyosin by direct immunological screening of a cDNA expression library", PNAS US 80, 1983, 31-35.

Kalisch, et al., "Covalently linked sequencing primer linkers (splinkers) for sequence analysis of restriction fragments", Gene 44, 1986, 263-270.

Kimmel, et al., "Preparation of cDNA and the Generation of cDNA Libraries: Overview", Methods in Enzymology 152, 1987, 307-316.

Kinzler, et al., Whole genome PCR: application to the identification of sequences bound by gene regulatory proteins, Nucleic Acids Research, 17(10), 1989, 3645-3653.

Lucito, et al., "Genetic analysis using genomic representations", PNAS, 95, 1998, 4487-4492.

Mardis, "next-generation DNA sequencing methods", Annual Review of Genomics and Human Genetics, Sep. 2008, 387-402.

Margulies, et al., "Genome sequencing in microfabricaled high-density picolilre reactors", Nature, vol. 437, 2005, 376-380 and Supplemental Materials.

Matsunaga, et al., "Selecting and amplifying one fragement from a DNA fragment mixture by polyermerase chain reaction with a pair of selective primers", Electrophoresis, vol. 17, 1996, 1833-1840.

Ng, et al., "Multiplex sequencing of paired-end ditags (MS-PET): a strategy for the ultra-high-throughput analysis of transcriplomes and genomes", Nucleic Acids research 2006—vol. 34 No. 12, Jul. 2006, E84.

Oroskar, et al., "Detection of immobilized amplicons by ELISA-like techniques", Clinical Chemistry 42, 1996, 1547-1555.

Roach, et al., "Pairwise end sequencing: A unified approach to genomic mapping and sequencing", Genomics 26, 1995, 345-353.

Saiki, et al., "Analysis of enzymatically amplified . . . -globin and HLA-DQ . . . DNA with allele-specific oligonucleolide ~robes", Nature 324, 1986, 163-166.

Saiki, et al., "Primer-Directed Enzymatic Amplification of DNA with a Thermostable DNA Polymerase", Science 239, 1988, 487-491.

San Luis, et al., "Analysis of a gene (vch) encoding hemolysin isolated and sequenced from Vibrio campbellii", Journal of general and Applied Microbiology; vol. 52; No. 6, Dec. 2006, 303-313.

Sanger, et al., "Cloning in Single-Stranded Bacteriophage as an Aid to Rapid DNA Sequencing", Mol Biologiy 143, 1980, 161-178.

Shapero, et al., "SNP Genotyping by multiplexed solid-phase amplification and fluorescent minisequencing", Genome Research vol. 11 No. 11, 2001, 1926-1934.

Shen Dure, et al., "Accurate Multiplex Polony Sequencing of an Evolved Bacterial Genome", Science, Sep. 9, 2005, 1728-1732.

Shendure, et al., "Next-generation DNA sequencing", Nature Biotechnology 26(10), 2008, 1135-1145.

(56) References Cited

OTHER PUBLICATIONS

Shi, "Enablling large-scale Pharmacogenetic studies by high-throughput mutation detection and genotyping technologies", Clinical Chemistry vol. 47 No 2, 2000, 164-172.
Solexa, "Solexa Application Note: DNA Sequencing", 2006.
Sterky, et al., "Direct sequencing of bacterial artificial chromosomes [bacS] prokaryotic genomes by biotin capture DCR", Journal of Biotechnology, vol. 60, 1998, 119-129.
Strick, et al., "Stress-Induced Structural Transistions of DNA and Proteins", Annu Rev. Biophys. Biomol. Strucl. 29, *JOOO*, 523-543.
Velculescu, et al., "Serial analysis of gene expression", Science, 270, 1995, 484-487.
Warren, Rene, et al., "Assembling Millions of short DNA sequences using Ssake", Bioinformatics (Oxford) vol. 23 No. 4, 2007, 500-501.
Westin, et al., "Anchored multiplex amplification on a microelectric chip array", Nature Biotechnology 18, 2000, 199-204.
Wiemann, et al., "Doublex Fluorescent DNA sequencing: two independent sequences obtained simultaneously in one reaction with internal labeling and unlabeled primers", Analytical Biochemistry US, 1996, 166-174.

\* cited by examiner

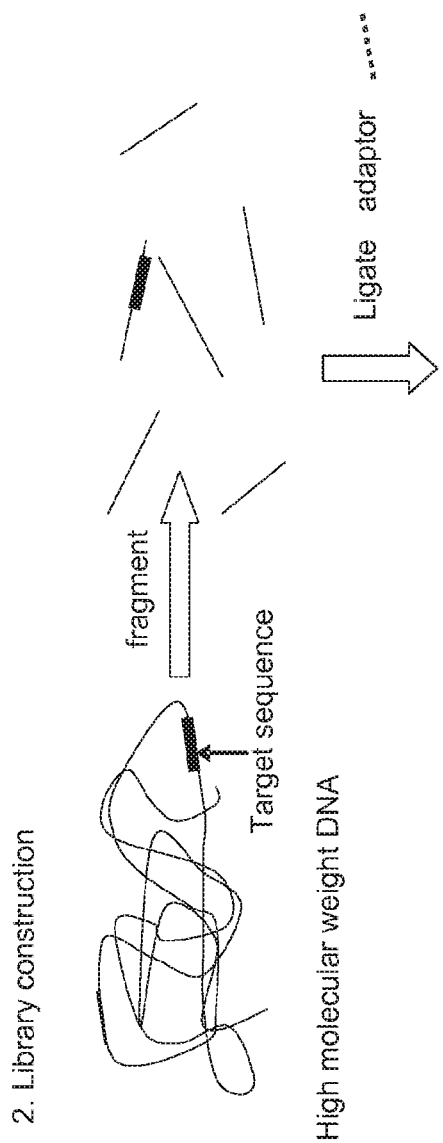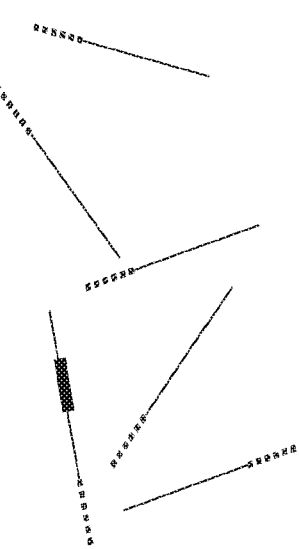
Fig 5

SEQUENCE LISTING

<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1
agagtttgat cctggctcag                                               20

<210> SEQ ID NO 2
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 2
aaggaggtga tccagccgca                                               20

<210> SEQ ID NO 3
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 3
actcctacgg gaggcagcag                                               20

<210> SEQ ID NO 4
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 4
ttaccgcggc tgctggcac                                                19

<210> SEQ ID NO 5
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 5
mwacgcgarr aaccttacc                                                19

<210> SEQ ID NO 6
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 6
cgacarccat gcascacct                                                19

METHOD FOR SELECTING AND AMPLIFYING POLYNUCLEOTIDES

CROSS-REFERENCE TO RELATED APPLICATIONS

This application is a continuation of U.S. application Ser. No. 16/786,198 filed Feb. 10, 2020 which is a continuation of U.S. application Ser. No. 15/489,549 filed Apr. 17, 2017 now U.S. Pat. No. 10,597,653 issued Mar. 24, 2020 which is a continuation of U.S. application Ser. No. 14/611,991 filed Feb. 2, 2015 now U.S. Pat. No. 9,624,489 issued Apr. 18, 2017 which is a continuation of U.S. application Ser. No. 13/387,078 filed Jan. 25, 2012 now U.S. Pat. No. 8,999,642 issued Apr. 7, 2015 which is the U.S. National Phase of Int. App. No. PCT/US2009/054945 filed Aug. 25, 2009 which is a continuation-in-part of U.S. application Ser. No. 12/395,299 filed Feb. 27, 2009 now abandoned which claims priority to U.S. Prov. App. No. 61/035,254 filed Mar. 10, 2008, which are each incorporated by reference in its entirety.

REFERENCE TO SEQUENCE LISTING

The present application is being filed along with a Sequence Listing in electronic format. The Sequence Listing is provided as a file entitled SEQLISTING ILLINC537C3, created Sep. 8, 2021, which is approximately 2 Kb in size. The information in the electronic format of the Sequence Listing is incorporated herein by reference in its entirety.

FIELD OF THE INVENTION

The current invention relates to the field of nucleic acid amplification. More specifically, the present embodiments provide methods for selecting one or more regions of a nucleic sample on a solid support and growing nucleic acid clusters directly on the solid support whilst eliminating the need for multiple sample titration steps.

BACKGROUND OF THE INVENTION

Several publications and patent documents are referenced in this application in order to more fully describe the state of the art to which this invention pertains. The disclosure in its entirety of each of these publications and documents is incorporated by reference herein.

A number of methods for high throughput nucleic acid sequencing rely on a universal amplification reaction, whereby a DNA sample is randomly fragmented, then treated such that the ends of the different fragments all contain the same DNA sequence. Fragments with universal ends can then be amplified in a single reaction with a single pair of amplification oligonucleotides. Separation of the library of fragments to the single molecule level prior to amplification ensures that the amplified molecules form discrete populations that can then be further analysed. Such separations can be performed either in emulsions, or on a surface. Alternatively it is possible to design amplification oligonucleotides which are specific to certain portions of the nucleic acid sample, and hence remove the need to modify the ends of the sample.

Polynucleotide arrays have been formed based on 'solid-phase' nucleic acid amplification. For example, a bridging amplification reaction can be used wherein a template immobilised on a solid support is amplified and the amplification products are formed on the solid support in order to form arrays comprised of nucleic acid clusters or 'colonies'. Each cluster or colony on such an array is formed from a plurality of identical immobilized polynucleotide strands and a plurality of identical immobilised complementary polynucleotide strands. The arrays so formed are generally referred to herein as 'clustered arrays.'

In common with several other amplification techniques, solid-phase bridging amplification uses forward and reverse amplification oligonucleotides which include 'template specific' nucleotide sequences which are capable of annealing to sequences in the template to be amplified, or the complement thereof, under the conditions of the annealing steps of the amplification reaction. The sequences in the template to which the primers anneal under conditions of the amplification reaction may be referred to herein as 'primer binding' sequences.

Certain embodiments of clustering methods make use of 'universal' primers to amplify a variable template portion that is to be amplified and that is flanked 5' and 3' by common or 'universal' primer binding sequences. The 'universal' forward and reverse primers include sequences capable of annealing to the 'universal' primer binding sequences in the template construct. The variable template portion, or 'target' may itself be of known, unknown or partially known sequence. This approach has the advantage that it is not necessary to design a specific pair of primers for each target sequence to be amplified; the same primers can be used for amplification of different templates provided that each template is modified by addition of the same universal primer-binding sequences to its 5' and 3' ends. The variable target sequence can therefore be any DNA fragment of interest. An analogous approach can be used to amplify a mixture of templates (targets with known ends), such as a plurality or library of target nucleic acid molecules (e.g., genomic DNA fragments), using a single pair of universal forward and reverse primers, provided that each template molecule in the mixture is modified by the addition of the same universal primer-binding sequences.

Such 'universal primer' approaches to PCR amplification, and in particular solid-phase bridging amplification, are advantageous since they enable multiple template molecules of the same or different, known or unknown sequence to be amplified in a single amplification reaction, which may be carried out on a solid support bearing a single pair of 'universal' primers. Simultaneous amplification of a mixture of templates of different sequences can otherwise be carried out with a plurality of primer pairs, each pair being complementary to each unique template in the mixture. The generation of a plurality of primer pairs for each individual template can be cumbersome and expensive for complex mixtures of templates. In certain applications such as detecting the presence of a viral or microbial infection, or for characterising a population of microbes, it may be possible to design the amplification oligonucleotides such that only the nucleic acid from the microbes is amplified.

In preparing a clustered array, typically the higher the concentration of template used, the higher the density of clusters that will be produced on a clustered array. If the density of clusters is too great, it may be difficult to individually resolve each cluster and overlapping colonies may be formed. A titration can be performed to determine the optimal template concentration to achieve an optimal cluster density on the array wherein each cluster can be separately resolved. However, such titrations can lead to a loss of valuable flow cell channels due to a cluster density that is too high or too low, a loss of template sample, an increase in the level of reagents required or an increase in sample processing time.

Thus, there is a need for a method of controlling and achieving desired cluster density that is independent of the concentration of the original nucleic acid sample and avoids nucleic acid titration steps. The present invention satisfies this need and provides other advantages as well

SUMMARY OF THE INVENTION

The invention provides in certain embodiments a method of selecting and amplifying polynucleotides. The method can include (a) providing a nucleic acid sample having a plurality of template polynucleotides; (b) providing a plurality of oligonucleotides immobilised on a solid support wherein the plurality of oligonucleotides includes (i) a plurality of capture oligonucleotides each having a different sequence capable of hybridising to a selected region of the nucleic acid sample, and (ii) a plurality of amplification oligonucleotides, wherein the capture oligonucleotides are immobilised at a lower density than the amplification oligonucleotides; (c) applying the template polynucleotides to the solid support under conditions such that the template polynucleotides selectively hybridise to the capture oligonucleotides; (d) extending the capture oligonucleotides to generate extension products complementary to the template polynucleotides; and (e) amplifying the extension products using the one or more amplification sequences immobilised on the solid support.

In a particular aspect, the invention provides a method of controlling the sequence and density of colonies of amplified single stranded polynucleotides formed on a solid support. The method can include the steps of (a) providing a plurality of template polynucleotides; (b) providing a plurality of at least three oligonucleotides immobilised to a solid support wherein at least one of the oligonucleotides is a capture oligonucleotide capable of hybridising to the template polynucleotides, and at least two of the oligonucleotides are amplification oligonucleotides which are incapable of hybridising to the template polynucleotides, wherein the capture oligonucleotides are immobilised at a lower density than the amplification oligonucleotides and the capture oligonucleotides are selective for a portion of the plurality of template polynucleotides; (c) applying the template polynucleotides to the solid support under suitable conditions such that the template polynucleotide molecules selectively hybridise to the capture oligonucleotides; (d) extending the capture oligonucleotides using a nucleic acid polymerase to generate double stranded extension products complementary to the single stranded template polynucleotides; (e) denaturing the double stranded extension products to remove the hybridised single stranded polynucleotide template molecules from the extension products to produce single stranded template molecules immobilised on the solid support; and (f) amplifying the single stranded template molecules immobilised on the solid support using the two or more amplification oligonucleotides immobilised on the solid support; wherein the density of the immobilised colonies is controlled by the density of the capture oligonucleotides rather than the concentration of the single stranded template polynucleotides.

The invention also provides in certain embodiments a flow cell uniformly grafted with a plurality of oligonucleotides, wherein the plurality includes four species of oligonucleotides having different sequences, wherein two of the four species (e.g., a first and a second species) are present at a lower density than the other two species (e.g., a third and a fourth species).

BRIEF DESCRIPTION OF THE DRAWINGS

FIG. 5 shows a nucleic acid sample fragmented into a plurality of polynucleotides containing a selected target region. Upon fragmentation, some fragments contain the target region, thereby providing templates for subsequent capture, while other fragments do not contain a target region and can not therefore become templates. The fragments may undergo ligation of an adapter at one end. The adapter may be complementary to, or the same as one of the amplification oligonucleotides on the support.

DETAILED DESCRIPTION OF THE INVENTION

The invention relates in certain embodiments to methods for selecting and controlling the density of different molecular species derivatized on a surface. In particular embodiments, the molecular species are nucleic acids having different sequences. The invention is particularly useful for controlling the density of nucleic acid clusters produced on a solid support. An advantage of the methods is the reduction or even elimination of the need for multiple sample titration steps for controlling density of molecules on surfaces. Another advantage of the invention is the ability to select a portion of the nucleic acid sample via sequence selective hybridisation to the capture oligonucleotide.

The methods set forth herein can be used with those described in U.S. application Ser. No. 12/395,229 including, for example, methods of controlling the density of clusters by using capture oligonucleotides on a solid support. In particular embodiments the methods set forth herein include the use of the capture oligonucleotides to select a subset of the nucleic acid sample, and hence control both the sequence of the clusters and the number, or density, of clusters on the support.

In embodiments wherein surfaces are derivatized with nucleic acids for subsequent formation of amplified clusters, the density of the cluster on the support can be controlled by the density of one of the immobilised primers used for capturing the template samples. The density of primers on every chip can be controlled during manufacturing, simply by the ratio of the capture oligonucleotides to the amplification oligonucleotides, and hence the density of clusters can be independent of the concentration or dilution of the template sample. For example, conditions can be used where the template sample is in a molar excess relative to primers, such that the density of clusters will be substantially the same even if the concentration of template is further increased. This concentration independence removes the need to accurately measure the initial concentration of double stranded template, and is independent of the accurate dilution of the sample. The density of clusters on multiple chips can be made substantially uniform by controlling the ratio and concentration of capture oligonucleotides to amplification oligonucleotides attached to the chip surface. Because primers can typically be synthesized and manipulated under more controlled conditions than template samples that are derived from different biological sources, the methods set forth herein provide increased reproducibility in creating cluster arrays. Further advantages are provided by creating pools of primers in a desired ratio that can be reused for creating multiple cluster arrays having reproducible density.

Figure 3:
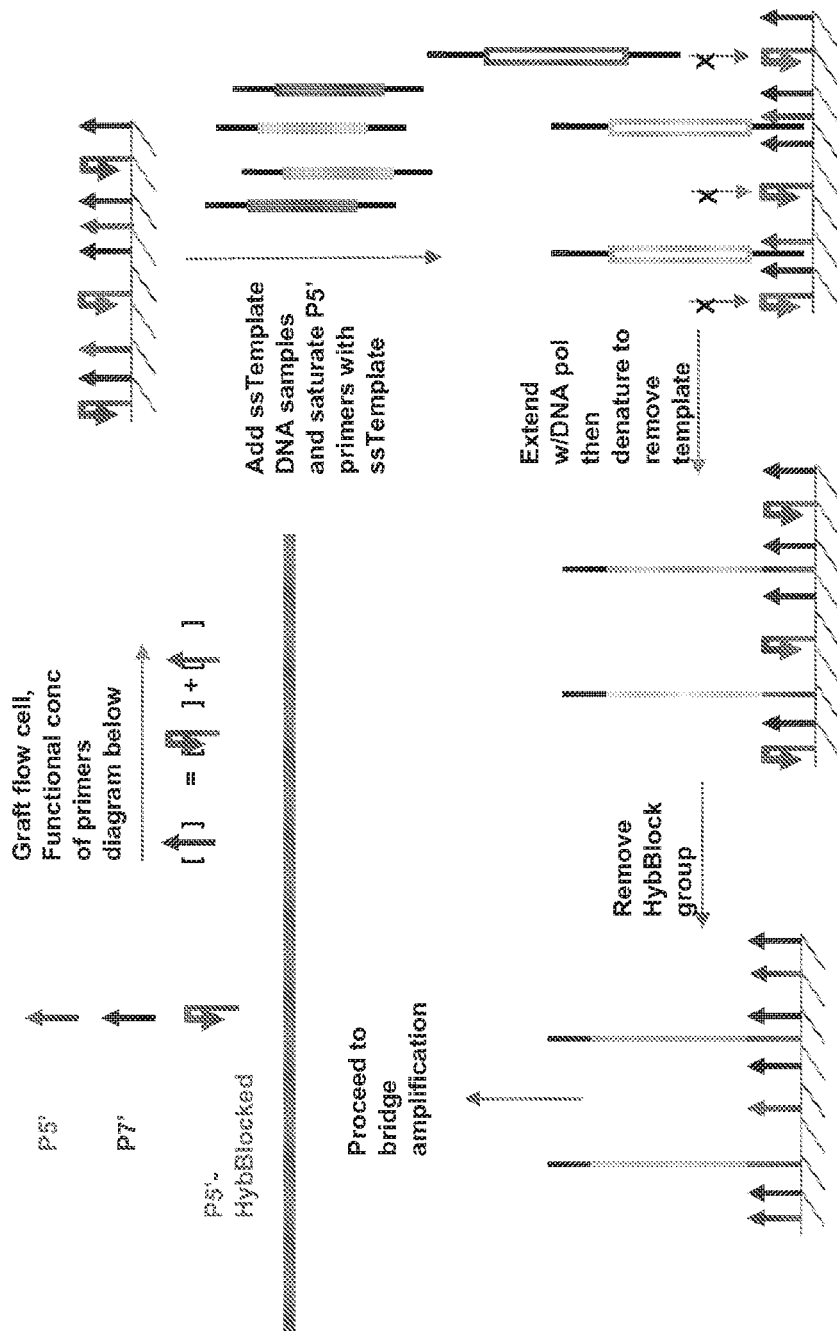
FIG. 3 shows an exemplary method of the invention wherein one of the amplification oligonucleotides is initially blocked from strand elongation. After extending the immobilised template strand, the block is removed and the sample can proceed through cycles of bridge amplification.
Figure 4:
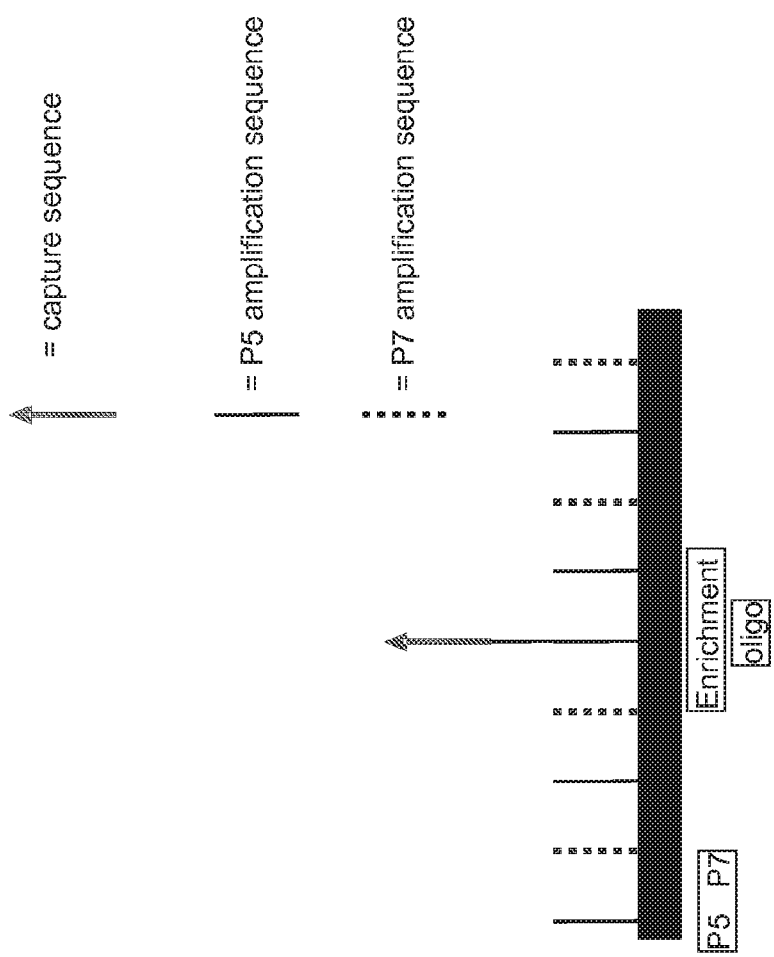
FIG. 4 shows an exemplary solid support with two different species of immobilised amplification oligonucleotides and one species of capture oligonucleotide.
Figure 6:
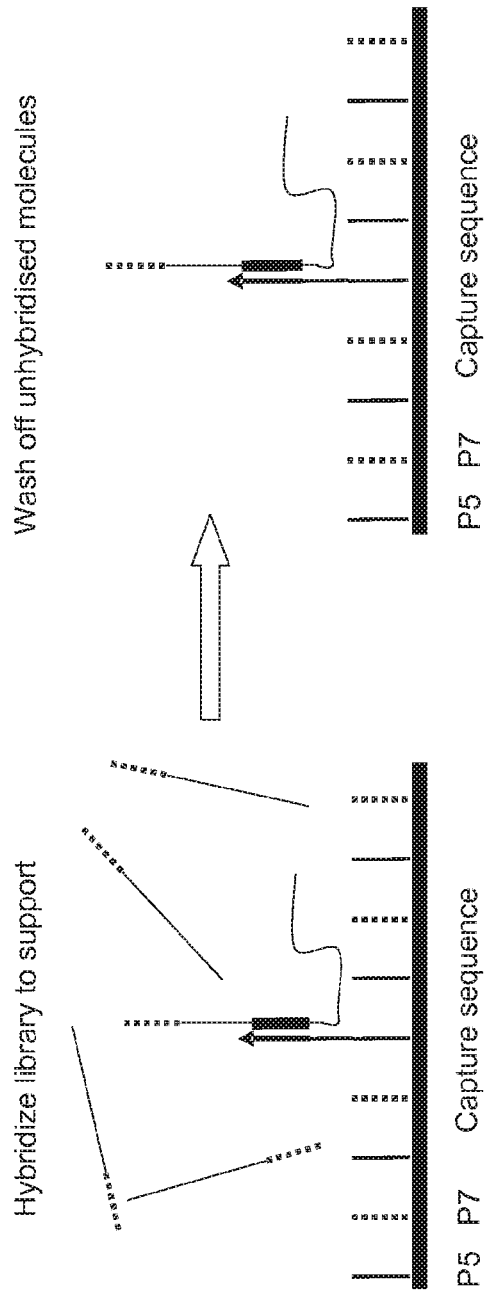
FIG. 6 shows hybridisation of a sample of template polynucleotides from FIG. 5 to a support. The sample hybridises to the capture oligonucleotide via the target region, and the remaining molecules in sample, which do not contain the target region do not hybridise and can be washed from the support. The molecules captured on the support can be used as template polynucleotides.
Figure 7:
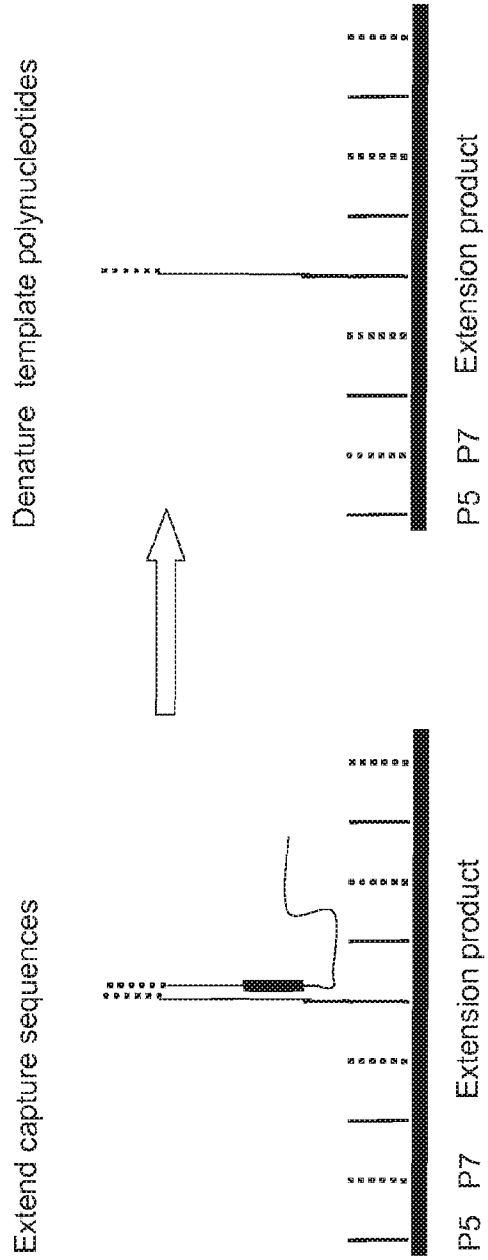
FIG. 7 shows that the capture oligonucleotides that have captured the template polynucleotides from FIG. 6 can be extended to make extension products complementary to the template polynucleotides. The template polynucleotides can be denatured. If the templates carry an adapter sequence, the adapter sequence is copied as part of the extension. If the copy of the adapter sequence is complementary to an amplification oligonucleotide, the extension products can be amplified using the amplification oligonucleotides on the support.
Figure 8:
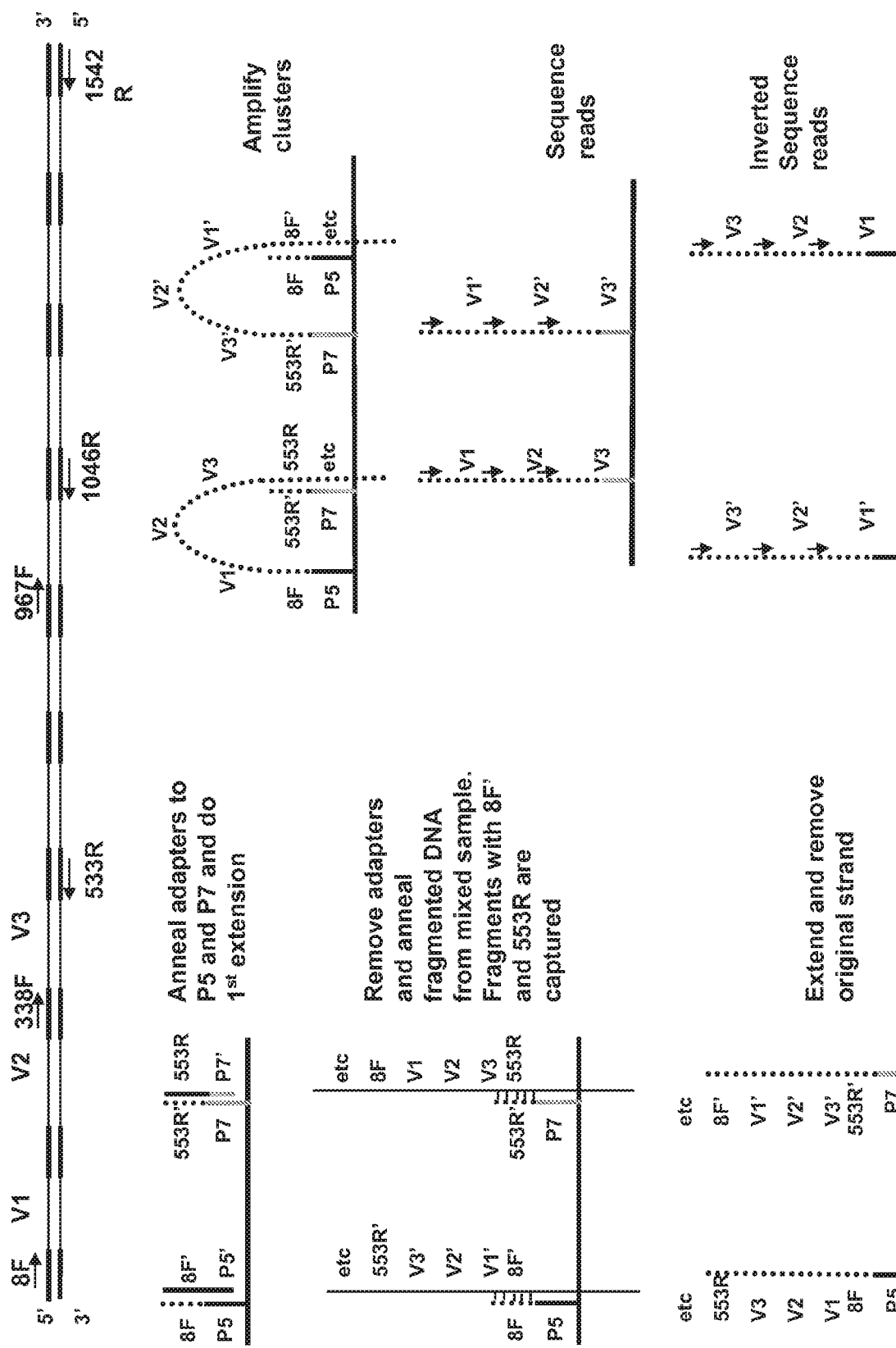
FIG. 8 shows an assay for analysing a population of microbes using 16S ribosomal RNA sequencing. The capture oligonucleotides on the support are shown as being selective for two of the constant regions of the bacterial 16S ribosomal RNA gene (8F and 553R). These two primers can be used to amplify approximately 500 base pairs of the approximately 1500 base pair gene, and include the V1, V2 and V3 variable regions. The capture oligonucleotides are produced by extension of the P5 and P7 amplification oligonucleotides. The capture oligonucleotides are then used to specifically capture the fragments of the 16S rRNA genes from the sample. The capture oligonucleotides are then extended. Each extended capture oligonucleotide can be turned into a cluster by solid phase amplification using the amplification oligonucleotides. Sequencing the clusters gives information about the members of the population of microbes due to the different 16S RNA regions captured and sequenced, as each microbe has a characteristic 16S gene sequence.

In accordance with the methods set forth herein a plurality of oligonucleotides can be immobilised to a solid support. The plurality can include different species of oligonucleotide molecule each having a different sequence. For example, a plurality of oligonucleotides can include at least two different species of oligonucleotides, at least three different species, at least four different species or more, wherein a first species has a different sequence than the other species in the plurality. It will be understood that different species of oligonucleotide can share a common sequence so long as there is a sequence difference between at least a portion of the different species. For example, as shown in FIG. 3, the two species identified as P5' and P5' HybBlocked share a common sequence but the P5' HybBlocked species has an additional hairpin forming sequence not found in the P5' species.

The term ' immobilised' as used herein is intended to encompass direct or indirect attachment to a solid support via covalent or non-covalent bond(s). In certain embodiments of the invention, covalent attachment may be used, but generally all that is required is that the molecules (for example, nucleic acids) remain immobilised or attached to a support under conditions in which it is intended to use the support, for example in applications requiring nucleic acid amplification and/or sequencing. Typically oligonucleotides to be used as capture oligonucleotides or amplification oligonucleotides are immobilised such that a 3' end is available for enzymatic extension and at least a portion of the sequence is capable of hybridizing to a complementary sequence. Immobilization can occur via hybridization to a surface attached oligonucleotide, in which case the immobilized oligonucleotide or polynucleotide may be in the 3'-5' orientation. Alternatively, immobilization can occur by means other than base-pairing hybridization, such as the covalent attachment set forth above.

The term 'solid support' as used herein refers to any insoluble substrate or matrix to which molecules can be attached, such as for example latex beads, dextran beads, polystyrene surfaces, polypropylene surfaces, polyacrylamide gel, gold surfaces, glass surfaces and silicon wafers. The solid support may be a planar glass surface. The solid support may be mounted on the interior of a flow cell to allow the interaction with solutions of various reagents.

In certain embodiments the solid support may comprise an inert substrate or matrix which has been 'functionalised', for example by the application of a layer or coating of an intermediate material comprising reactive groups that permit covalent attachment to molecules such as polynucleotides. By way of non-limiting example such supports may include polyacrylamide hydrogel layers on an inert substrate such as glass. In such embodiments the molecules (for example, polynucleotides) may be directly covalently attached to the intermediate layer (for example, a hydrogel) but the intermediate layer may itself be non-covalently attached to other layers of the substrate or matrix (for example, a glass substrate). Covalent attachment to a solid support is to be interpreted accordingly as encompassing this type of arrangement.

'Primer oligonucleotides' or Amplification oligonucleotides' are oligonucleotide sequences that are capable of annealing specifically to a single stranded polynucleotide sequence to be amplified under conditions encountered in a primer annealing step of an amplification reaction. Generally, the terms 'nucleic acid, 'polynucleotide' and Oligonucleotide' are used interchangeably herein. The different terms are not intended to denote any particular difference in size, sequence, or other property unless specifically indicated otherwise. For clarity of description the terms may be used to distinguish one species of molecule from another when describing a particular method or composition that includes several molecular species.

A polynucleotide sequence that is to be copied or amplified is generally referred to herein as a 'template.' A template can include primer binding sites that flank a template sequence that is to be amplified. A template hybridised to a capture oligonucleotide may contain bases which extend beyond the 5' end of the capture oligonucleotide in such a way that not all of the template is amenable to extension. In particular embodiments, as set forth in further detail below, a plurality of template polynucleotides includes different species that differ in their template sequences but have primer binding sites that are the same for two or more of the different species. The two primer binding sites which may flank a particular template sequence can have the same sequence, such as a palindromic sequence or homopolymeric sequence, or the two primer binding sites can have different sequences. Accordingly, a plurality of different template polynucleotides can have the same primer binding sequence or two different primer binding sequences at each end of the template sequence. Thus, species in a plurality of template polynucleotides can include regions of known sequence that flank regions of unknown sequence that are to be evaluated, for example, by sequencing. Template polynucleotides may carry a single adapter species to serve as a primer binding sequence at a single end only. In cases where the templates carry an adapter at a single end, this may be either the 3' end or the 5' end. Template polynucleotides may be used without any adapter, in which case the primer binding sequence comes directly from a sequence found in the nucleic acid sample.

Generally amplification reactions use at least two amplification oligonucleotides, often denoted 'forward' and 'reverse' primers. Generally amplification oligonucleotides are single stranded polynucleotide structures. They may also contain a mixture of natural or non-natural bases and also natural and non-natural backbone linkages, provided, at least in some embodiments, that any non-natural modifications do not permanently or irreversibly preclude function as a primer—that being defined as the ability to anneal to a template polynucleotide strand during conditions of an extension or amplification reaction and to act as an initiation point for the synthesis of a new polynucleotide strand complementary to the annealed template strand. That being said, in certain embodiments the present invention may involve the use of a subset of primers, either forward or reverse, that have been modified to preclude hybridisation to a template polynucleotide strand, the modification being altered or reversed at some point such that hybridisation is no longer precluded.

Primers may additionally comprise non-nucleotide chemical modifications, for example to facilitate covalent attachment of the primer to a solid support. Certain chemical modifications may themselves improve the function of the molecule as a primer or may provide some other useful functionality, such as providing a cleavage site that enables the primer (or an extended polynucleotide strand derived therefrom) to be cleaved from a solid support. Useful chemical modifications can also provide reversible modifications that prevent hybridisation or extension of the primer until the modification is removed or reversed. Similarly, other molecules attached to a surface in accordance with the invention can include cleavable linker moieties and or reversible modifications that alter a particular chemical activity of function of the molecule.

Figure 1:
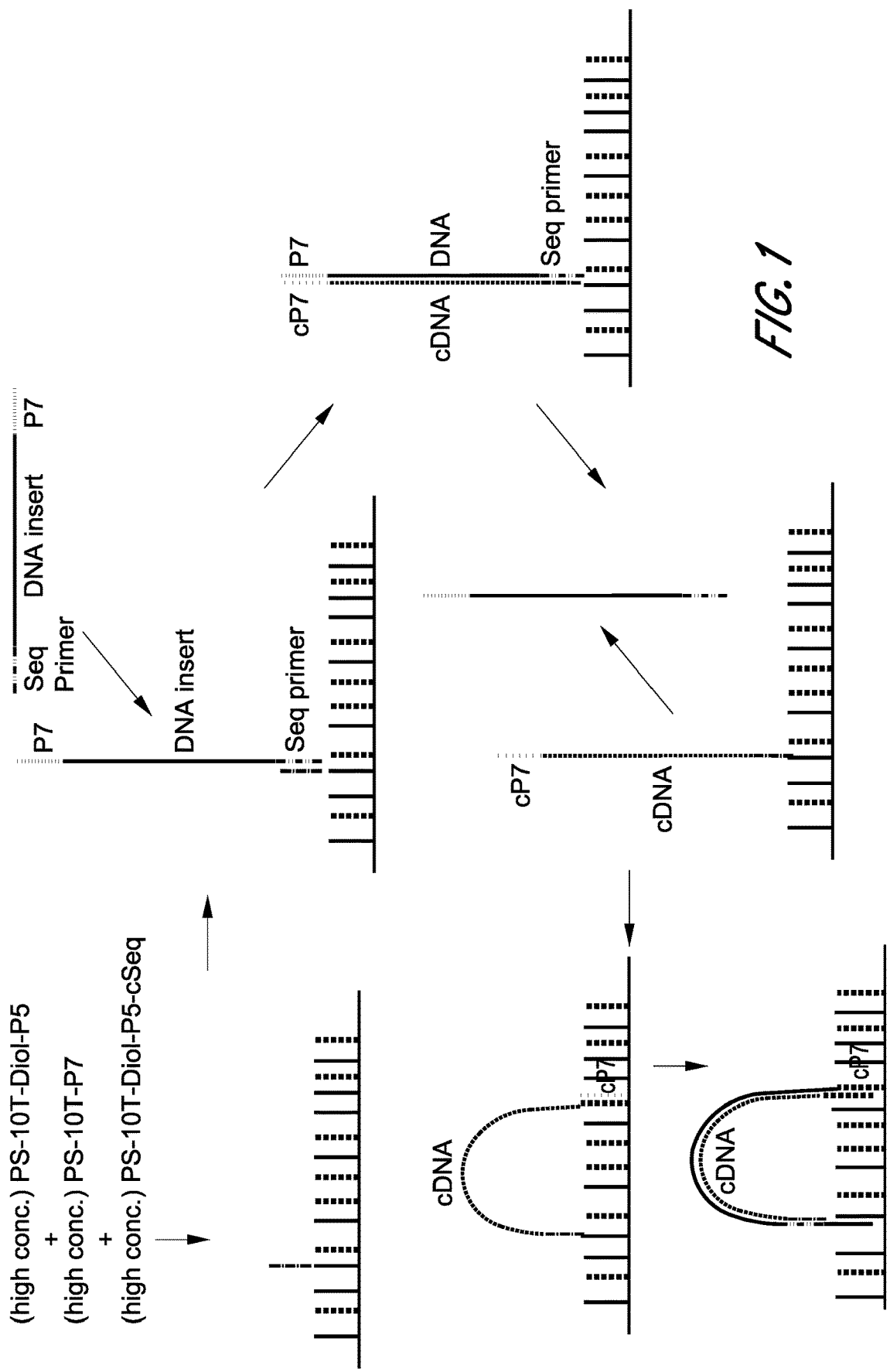
FIG. 1 shows a method of the invention wherein the capture oligonucleotide is longer than the amplification oligonucleotides, and the template selectively hybridises to the capture oligonucleotide that extends beyond the amplification oligonucleotide. The capture oligonucleotide is extended opposite the template strand, and the template strand is denatured and removed. The immobilised template copy can hybridise to one of the immobilised amplification oligonucleotides, and the amplification oligonucleotide can be extended. The capture oligonucleotide also comprises a sequence corresponding to one of the amplification oligonucleotides, and hence upon synthesising a duplex from the immobilised template copy, both ends of the immobilised duplex can comprise sequences complementary to one of the amplification oligonucleotides.

A plurality of oligonucleotides used in the methods set forth herein can include species that function as capture oligonucleotides. The capture oligonucleotides may include a 'template specific portion', namely a sequence of nucleotides capable of annealing to a selected region of the nucleic acid sample in a polynucleotide molecule of interest such as one that is to be amplified. The capture oligonucleotides may comprise a sequence which is specific for a subset of the molecules in a nucleic acid sample. Thus only a subset of the molecules in the sample may in these and related embodiments be selected by the capture oligonucleotides to become template polynucleotides. The capture oligonucleotides may comprise a single species of oligonucleotide, or may comprise two or more species with a different sequence. Thus the capture oligonucleotide may be two or more sequences, 10 or more sequences, 100 or more sequences, 1000 or more sequences or 10000 or more sequences. The primer binding sequences will generally be of known sequence and will therefore be complementary to a region of known sequence of the single stranded polynucleotide molecule. The capture oligonucleotides may include a capture oligonucleotide and an amplification oligonucleotide. For example, as shown in FIG. 1, a capture oligonucleotide may be of greater length than amplification oligonucleotides that are attached to the same substrate, in which case the 5' end of the capture oligonucleotides may comprise a region with the same sequence as one of the amplification oligonucleotides. A portion of a template, such as the 3' end of the template, may be complementary to the 3' of the capture oligonucleotides. The 5' end of the template may contain a region that comprises a sequence identical to one of the amplification oligonucleotides such that upon copying the template, the copy can hybridise to the immobilized amplification oligonucleotide. Thus, an oligonucleotide species that is useful in the methods set forth herein can have a capture oligonucleotide, an amplification oligonucleotide or both. Conversely, an oligonucleotide species can lack a capture oligonucleotide, an amplification oligonucleotide or both. In this way the hybridization specificity of an oligonucleotide species can be tailored for a particular application of the methods.

The length of primer binding sequences need not be the same as those of known sequences of polynucleotide template molecules and may be shorter in certain embodiments, for example, being particularly 16-50 nucleotides, more particularly 16-40 nucleotides and yet more particularly 20-30 nucleotides in length. The desired length of the primer oligonucleotides will depend upon a number of factors. However, the primers are typically long (complex) enough so that the likelihood of annealing to sequences other than the primer binding sequence is very low. Accordingly, known sequences that flank a template sequence can include a primer binding portion and other portions such as a capture oligonucleotide, tag sequence or combination thereof.

'Solid phase amplification,' when used in reference to nucleic acids, refers to any nucleic acid amplification reaction carried out on or in association with a solid support. Typically, all or a portion of the amplified products are synthesised by extension of an immobilised primer. In particular the term encompasses solid phase amplification reactions analogous to standard solution phase amplifications except that at least one of the amplification oligonucleotides is immobilised on the solid support.

As will be appreciated by the skilled reader, a given nucleic acid amplification reaction can be carried out with at least one type of forward primer and at least one type of reverse primer specific for the template to be amplified. However, in certain embodiments, the forward and reverse primers may include template specific portions of identical sequence. In other words, it is possible to carry out solid phase amplification using only one type of primer and such single primer methods are encompassed within the scope of the invention. The one type of primer may include (a) subset (s) of modified primer (s) that have been modified to preclude hybridisation to a template polynucleotide strand, the modification being removed, altered or reversed at some point such that hybridisation is no longer precluded. Other embodiments may use forward and reverse primers which contain identical template specific sequences but which differ in some structural features. For example, one type of primer may contain a non-nucleotide modification which is not present in the other. In still yet another embodiment, the template specific sequences are different and only one primer is used in a method of linear amplification. In other embodiments of the invention the forward and reverse primers may contain specific portions of different sequence.

In certain embodiments of the invention, amplification oligonucleotides for solid phase amplification are immobilised by covalent attachment to the solid support at or near the 5' end of the primer, such that a portion of the primer is free to anneal to its cognate template and the 3' hydroxyl group is free to function in primer extension. Again, in certain embodiments there is provided a subset of modified primers that are prevented from hybridisation and/or extension until the modification is removed, reversed or altered. In particular embodiments, the amplification oligonucleotides will be incapable of hybridisation to the initial single stranded template. In such embodiments, hybridisation of the single stranded template will typically be specific for the capture oligonucleotides such that the amount of capture oligonucleotides on the surface determines the amount of template captured and thus the density of the resulting amplified clusters.

The chosen attachment chemistry will typically depend on the nature of the solid support and any functionalization or derivatization applied to it. In the case of nucleic acid embodiments, the primer itself may include a moiety which may be a non-nucleotide chemical modification to facilitate attachment. For example, the primer may include a sulphur containing nucleophile such as a phosphorothioate or thiophosphate at the 5' end. In the case of solid supported polyacrylamide hydrogels, this nucleophile may bind to a bromoacetamide group present in the hydrogel. In one embodiment, the means of attaching primers to the solid support is via 5' phosphorothioate attachment to a hydrogel comprised of polymerized acrylamide and N-(5-bromoacetamidylpentyl) acrylamide (BRAPA).

A uniform, homogeneously distributed 'lawn' of immobilised oligonucleotides may be formed by coupling (grafting) a solution of oligonucleotide species onto the solid support. The solution can contain a homogenous population of oligonucleotides but will typically contain a mixture of different oligonucleotide species. The mixture can include, for example, at least two, three or more different species of oligonucleotide. Each surface that is exposed to the solution therefore reacts with the solution to create a uniform density of immobilised sequences over the whole of the exposed solid support. As such, a portion of the surface having a mixture of different immobilized sequences can be surrounded by an area of the surface having a mixture of the same immobilized sequences. A suitable density of amplification oligonucleotides is at least 1 fmol/mm$^2$ ($6 \times 10^{10}$ per cm$^2$), or more optimally at least 10 fmol/mm$^2$ ($6 \times 10^{11}$ per cm$^2$). The density of the capture oligonucleotides can be controlled to give an optimum cluster density of $10^6$-$10^9$ clusters per cm$^2$. The ratio of capture oligonucleotide species to the amplification oligonucleotide species can be any desired value including, but not limited to at least 1:100, 1:1000 or 1:100000 depending on the desired cluster density and brightness. Similar densities or ratios of other molecular species can be used in embodiments where molecules other than nucleic acids are attached to a surface.

Capture oligonucleotides may be deposited on the solid support at the same time as the amplification oligonucleotides. Alternatively, especially in situations where the template polynucleotides do not carry sequences complementary to the amplification oligonucleotides, the capture oligonucleotides may be produced using a solid support carrying only amplification oligonucleotides by extending a portion of the amplification oligonucleotides using a copy of the capture oligonucleotides as a template. For example, a population of oligonucleotide probes which contain a sequence complementary to one of the amplification oligonucleotides and a sequence which extends beyond the amplification oligonucleotides may be prepared. This population of oligonucleotides may be hybridised to the amplification oligonucleotides on the support at a sufficiently low density that only a portion of the amplification oligonucleotides on the support become hybridised. For example, the hybridised molecules might be individually resolvable such that the average distance between neighbouring molecules is large enough that the two molecules can be detected separately by optical microscopy. The portion of the amplification oligonucleotides with hybridised molecules may then undergo extension, e.g., using a polymerase and nucleoside triphosphates. This has the advantage that the capture oligonucleotides can be produced from a standard common solid support containing only the amplification oligonucleotides, i.e., the same solid support can be prepared for use in all applications without needing to manufacture a different support each time the sequence of the capture oligonucleotides is altered; and the capture oligonucleotides designed separately and added to the support.

Previously, the density of attached single stranded polynucleotide molecules and hence the density of clusters has been controlled by altering the concentration of template polynucleotide molecules applied to a support. By utilising a modified primer or capture oligonucleotide as set forth herein, the density of clusters on the amplified array can be controlled without relying on careful titration of the starting concentration of template polynucleotide strand applied to the solid support. This has the significant advantage that the methods need not rely on accurate concentration measurements and dilutions of the template polynucleotide molecules, thereby leading to increased reliability, reduction in dilution errors and a reduction in time and quantity of reagents required in downstream processes. For each solid support that contains too many or too few clusters, there is a reduction in the amount of data generated for an analysis of the clusters. This can mean that generating the required depth of coverage of the sample may require additional analytical runs that would not be required if the cluster density was optimal. Too many clusters gives optical saturation and an increase in overlap between two amplified molecules; too few clusters gives undesirably high amounts of dark space that do not generate any data, thereby wasting reagents that are more efficiently used with a densely populated surface.

In a particular embodiment, for each cluster, an immobilised complementary copy of a single stranded polynucleotide template molecule is attached to the solid support by a method of hybridisation and primer extension. Methods of hybridisation for formation of stable duplexes between complementary sequences by way of Watson-Crick base-pairing are known in the art. The immobilised capture oligonucleotides can include a region of sequence that is complementary to a region or template specific portion of the single stranded template polynucleotide molecule. An extension reaction may then be carried out wherein the capture oligonucleotide is extended by sequential addition of nucleotides to generate a complementary copy of the single stranded polynucleotide sequence attached to the solid support via the capture oligonucleotide. The single stranded polynucleotide sequence not immobilised to the support may be separated from the complementary sequence under denaturing conditions and removed, for example by washing.

The terms 'separate' and Separating,' when used in reference to strands of a nucleic acid, refer to the physical dissociation of the DNA bases that interact within for example, a Watson-Crick DNA-duplex of the single stranded polynucleotide sequence and its complement. The terms also refer to the physical separation of these strands. Thus, the term can refer to the process of creating a situation wherein annealing of another primer oligonucleotide or polynucleotide sequence to one of the strands of a duplex becomes possible. After the first extension reaction, the duplex is immobilised through a single 5' attachment, and hence strand separation can result in loss of one of the strands from the surface. In cases where both strands of the duplex are immobilised, separation of the strands means that the duplex is converted into two immobilised single strands.

In one aspect of the invention, one or more of the amplification oligonucleotides can be modified to prevent hybridisation of a region or template specific portion of the single stranded polynucleotide molecule. Alternatively or additionally, one or more of the amplification oligonucleotides may be modified to prevent extension of the primer during one or more extension reactions, thus preventing copying of the hybridised templates. These modifications can be temporary or permanent.

Generally, the capture oligonucleotides will include a region of the same sequence as the plurality of amplification oligonucleotides. Once the 3' end of the extended immobilised template copy has hybridised to one of the amplification oligonucleotides and been extended, the resulting duplex will be immobilised at both ends and all of the bases in the capture oligonucleotide sequence will have been copied. Thus the capture oligonucleotide may include both the amplification oligonucleotide sequence, plus a further sequence that is complementary to the end or central region of the template. Typically the sequence complementary to the template will not be present in any of the amplification oligonucleotides. Alternatively, the amplification oligonucleotides can contain the sequences complementary to the templates, but the amplification oligonucleotides can be reversibly blocked to prevent hybridisation and/or extension during one or more extension step, such as a first extension step in a particular amplification process.

According to one aspect of the invention, one or more of the amplification oligonucleotides may include a modification that acts as a reversible block to either template hybridisation or extension or both. By way of non-limiting example, such modifications may be manifest as the presence of an additional sequence of nucleotides that is complementary to the amplification oligonucleotide. This additional sequence can be present in a portion of the amplification oligonucleotide and thus acts as an intramolecular hairpin duplex, or a 3' blocking group that prevents extension of the primer. Alternatively, the additional sequence may be found on a separate oligonucleotide that hybridizes to the amplification oligonucleotide. A particular feature of such a modification is that it can be removed, altered or reversed such that the functionality of the modified primer oligonucleotide is restored and the primer is able to undergo hybridisation and extension during later steps of the methods. Among other examples, the blocking group may be a small chemical species such as a 3' phosphate moiety that can be removed enzymatically, may be an abasic nucleotide such that the 3' end of the primer is not capable of hybridisation (and thereby extension), or may be a sequence of nucleotides that can be selectively excised from the immobilised strands, for example, using restriction endonucleases that selectively cleave particular sequences or deglycosylases that selectively cleave oligonucleotides having exogenous bases such as uracil deoxyribonucleotides or 8-oxoguanine.

In one embodiment a plurality of three types of oligonucleotides (for example comprising capture oligonucleotides, forward and reverse amplification oligonucleotides) are immobilised to a solid support.

Alternatively the three oligonucleotides may be forward amplification, blocked forward amplification and reverse amplification, where the unblocked forward primer acts as the capture oligonucleotide.

The nucleic acid sample may be double or single stranded. In order to obtain effective hybridisation, the double stranded sample may be denatured to form single stranded polynucleotide molecules. The single stranded polynucleotide molecules may have originated in single-stranded form, as DNA or RNA or may have originated in double-stranded DNA (dsDNA) form (e.g., genomic DNA fragments, PCR and amplification products and the like). Thus a single stranded polynucleotide may be the sense or anti-sense strand of a polynucleotide duplex. Methods of preparation of single stranded polynucleotide molecules suitable for use in the method of the invention using standard techniques are well known in the art. The precise sequence of the primary polynucleotide molecules may be known or unknown during different steps of the methods set forth herein. It will be understood that a double stranded polynucleotide molecule can be hybridized to an immobilized capture oligonucleotide as exemplified herein for single stranded polynucleotide molecules, so long as a single stranded region of the double stranded polynucleotide is available and complementary to the capture oligonucleotide sequence.

Figure 2:
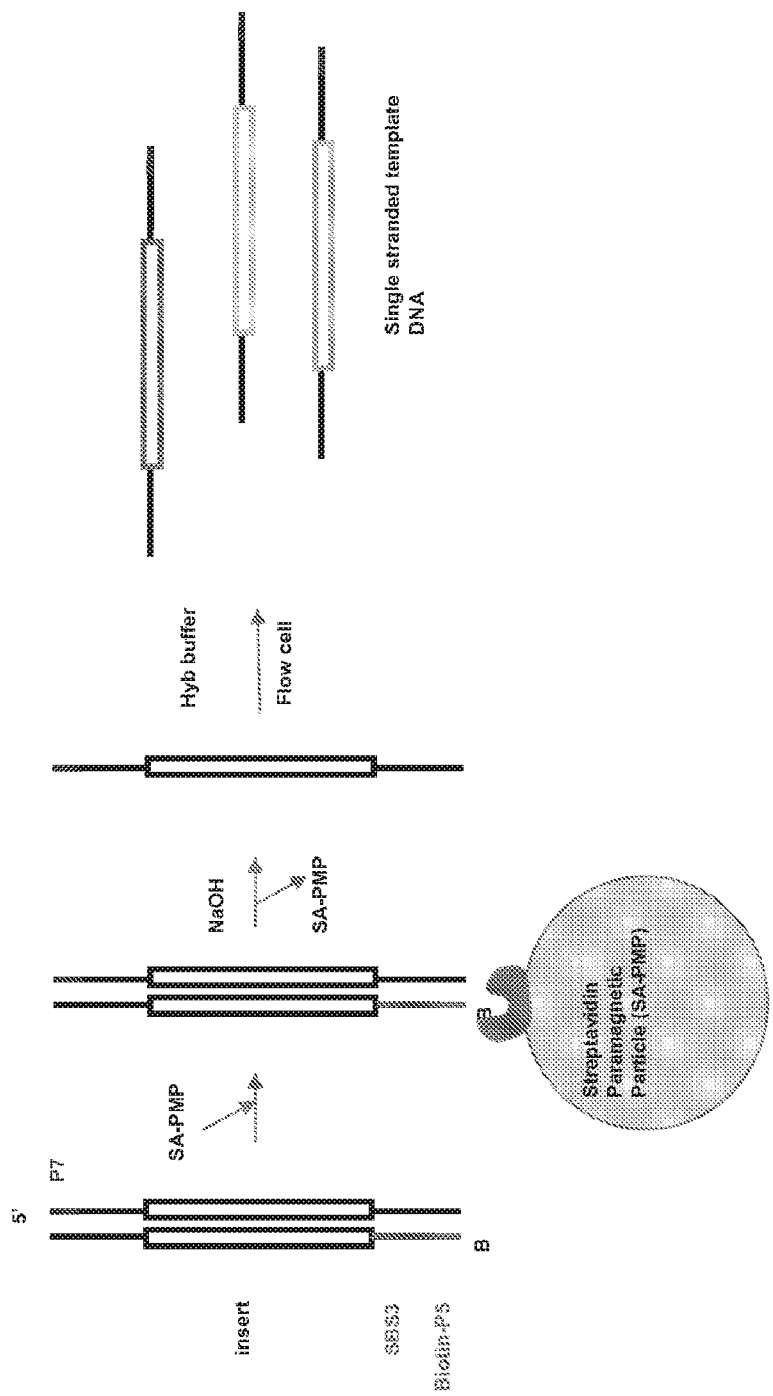
FIG. 2 shows an exemplary method of preparing a single stranded template library suitable for amplification.

An exemplary method for the isolation of one strand of a double stranded molecular construct is shown in FIG. 2. A sample of unknown sequence may be fragmented, and adapters attached to the ends of each fragment. One strand of the adapters may contain a moiety for surface immobilisation, for example a biotin that can be captured onto a streptavidin surface. The adapters may be mismatch adapters, for example as described in copending application US 2007/0128624, the contents of which are incorporated herein by reference in their entirety. Amplification of the mismatch or forked adapters using a pair of amplification oligonucleotides, one of which carries a biotin modification means that one strand of each duplex carries a biotin modification. Immobilisation of the strands onto a streptavidin surface means that the non-biotinylated strand can be eluted simply by denaturation/strand separation. The eluted constructs will be in single stranded form and upon exposure to hybridisation conditions can be used to hybridise against the immobilised capture oligonucleotides which can be extended.

In a particular embodiment, the single stranded polynucleotide molecules are DNA molecules. More particularly, the single stranded polynucleotide molecules represent genomic DNA molecules, or amplicons thereof, which include both intron and exon sequence (coding sequence), as well as non-coding regulatory sequences such as promoter and enhancer sequences. Still yet more particularly, the single stranded polynucleotide molecules are human genomic DNA molecules, or amplicons thereof.

In a particular embodiment, the nucleic acid molecules may be isolated from a biological sample that comprises a mixture of different organisms. For example, the sample may contain or include a mixture of different bacteria or viruses, such as may be present in cells, tissues or fluids of an individual organism, which may in certain embodiments be a human or other vertebrate. In order to work out which microbes are present in the sample, the 'microbiome', regions of the sample specific to bacteria may be sequenced, for example the 16S ribosomal RNA gene region from the DNA sample. Thus the amplification oligonucleotides, or the capture oligonucleotide may be selective for one of the constant regions found across the 16S rRNA gene region for all bacteria or the 18S gene region common across different eukaryotes.

An embodiment of the method described herein may be used to select and form clusters from the bacterial 16S ribosomal gene of any bacteria. Suitable bacteria may include (but are not intended to be limited to) *Acinetobacter baumannii, Actinomyces odontolyticus, Bacillus cereus, Bacteroides vulgatus, Clostridium beijerinckii, Deinococcus radiodurans, Enterococcus faecalis, Escherichia coli, Helicobacter pylori, Lactobacillus gasseri, Listeria monocytogenes, Methanobrevibacter smithii, Neisseria meningitides, Propionibacterium acnes, Pseudomonas aeruginosa, Rhodobacter sphaeroides, Staphylococcus aureus, Staphylococcus epidermidis, Streptococcus agalactiae, Streptococcus mutans* and *Streptococcus pneumoniae*.

The sample, for example a sample obtained from human gut, stool, saliva or skin, may be treated to extract the nucleic acid present in the sample. The total nucleic acid extracted from the sample may undergo fragmentation and may be contacted with a solid support carrying amplification and capture oligonucleotides as described herein. If individual capture oligonucleotides carry a region of sequence that is complementary to a gene sequence shared between all bacteria, then the bacterial nucleic acids will be captured, and the other nucleic acids, for example viral or human nucleic acids will not. The bacterial nucleic acids can then be amplified to form clusters. Variable regions of the captured nucleic acids can be detected, for example, by sequencing. The sequence of the variable regions provide information that can be used to identify the bacteria from which they were obtained. Upon sequencing the clusters, the ratio between the numbers of two or more bacteria in a sample may be calculated by counting the number of times a particular sequence read is obtained across the millions of clusters on the solid support.

Specific amplification of the bacterial sample is possible if the amplification oligonucleotides are only complementary to the bacterial nucleic acid. The capture oligonucleotides may be modified to select nucleic acids from a particular bacteria or virus. Multiple different capture oligonucleotides may be used in order to optimise selection of nucleic acid from the desired organism.

Capture oligonucleotides for selecting 16S gene regions may contain the following sequences:

| Name | Region | 5'-3' | SEQ ID NO: |
|---|---|---|---|
| 8F | Before V1 | AGAGTTTGATCCTGGCTCAG | 1 |
| 1542R | After V9 | AAGGAGGTGATCCAGCCGCA | 2 |

| Name | Region | 5'-3' | SEQ ID NO: |
|---|---|---|---|
| 338F | Before V3 | ACTCCTACGGGAGGCAGCAG | 3 |
| 533R | After V3 | TTACCGCGGCTGCTGGCAC | 4 |
| 967F | Before V6 | MWACGCGARRAACCTTACC | 5 |
| 1046R | After V6 | CGACARCCATGCASCACCT | 6 |

Wherein M, W, R and S are the standard degenerate base codes (M=A and/or C, W=A and/or T, R=G and/or A, and S=G and/or C).

The capture oligonucleotides may be attached directly to the amplification oligonucleotides, for example by preparing oligonucleotides containing both the amplification and capture oligonucleotides in a single construct and attaching this to a solid support. Alternatively the capture oligonucleotides may be prepared by attaching amplification oligonucleotides to a support and hybridising an oligonucleotide with a sequence complementary to the sequence of the capture oligonucleotide and the sequence of the amplification oligonucleotide to the amplification oligonucleotide. The complementary oligonucleotides can act as templates for the preparation of the capture oligonucleotides by extension of the amplification oligonucleotides.

In a particular embodiment, a single stranded target polynucleotide molecule has two regions of known sequence. Yet more particularly, the regions of known sequence will be at the 5' and 3' termini of the single stranded polynucleotide molecule such that the single stranded polynucleotide molecule will be of the structure:

5' [known sequence I]-[target polynucleotide sequence]-[known sequence II]-3'

Typically 'known sequence I' and 'known sequence II' will comprise more than 20, or more than 40, or more than 50, or more than 100, or more than 300 consecutive nucleotides. The precise length of the two sequences may or may not be identical. The primer binding sequences generally will be of known sequence and will therefore particularly be complementary to a sequence within known sequence I and known sequence II of the single stranded polynucleotide molecule. The length of the primer binding sequences need not be the same as those of known sequence I or II, and may be shorter, being particularly 16-50 nucleotides, more particularly 16-40 nucleotides and yet more particularly 20-30 nucleotides in length. Known sequence I can be the same as known sequence II or the two can be different.

Methods of hybridisation for formation of stable duplexes between complementary sequences by way of Watson-Crick base pairing are known in the art. A region or part of the single stranded polynucleotide template molecules can be complementary to at least a part of the immobilised capture oligonucleotide oligonucleotides. The plurality of polynucleotides from the sample which do not act as templates due to non-hybridisation with the capture oligonucleotides may be removed from the solid support, for example by washing or other form of fluid flow. Since the amplification oligonucleotides are either modified to prevent hybridisation and/or extension, or are non-complementary to the template strands, only the capture oligonucleotides will be capable of hybridisation and extension. An extension reaction may then be carried out wherein the capture oligonucleotide is extended by sequential addition of nucleotides to generate an extension product which is a complementary copy of the single stranded template polynucleotide attached to the solid support via the capture oligonucleotide. The single stranded template polynucleotide sequence not immobilised to the support may be separated from the complementary sequence under denaturing conditions and removed, for example by washing. The distance between the individual capture oligonucleotide on the surface therefore controls the density of the single stranded template polynucleotides and hence the density of clusters formed later on the surface is also controlled.

In embodiments such as that shown in FIG. 3 wherein the modified forward primer oligonucleotides are blocked and are unable to be extended, generally all of the amplification oligonucleotides will hybridise to the single stranded template polynucleotides. When the extension reaction is carried out only the unmodified forward capture oligonucleotides are extended by sequential addition of nucleotides to generate a complementary copy of the single stranded template polynucleotide attached to the solid support via the unmodified forward primer oligonucleotide. The single stranded template polynucleotide sequences not hybridised to the support may be separated from the un-extended blocked forward primer oligonucleotides under denaturing conditions and removed, for example by washing with a chemical denaturant such as formamide. The distance between the individual unmodified forward primer oligonucleotides on the surface therefore controls the density of the single stranded template polynucleotides and hence the density of clusters formed later on the surface is also controlled.

Following the attachment of the complementary single stranded template polynucleotides, the modified/blocked primers can be treated to reverse, remove or alter the modification such that they become functionally equivalent to the unmodified forward primer oligonucleotides. For example, the double stranded structure may be removed either by denaturation, for example by heating or treatment with an alkaline solution when it is formed by a separate hybridised polynucleotide. Alternatively, where the hybridised polynucleotide is covalently linked, enzymatic digestion could be used to sequence-selectively cleave the strand, followed by denaturation. Such methods for removing the double stranded structure are known in the art and would be apparent to the skilled person (Sambrook and Russell, *Molecular Cloning, A Laboratory Manual*, third edition, Cold Spring Harbor Laboratory Press (2001)).

In one embodiment of the invention, the single stranded template polynucleotide molecule can be attached to the solid support by ligation to double stranded primers immobilised to the solid support using ligation methods known in the art (Sambrook and Russell, supra). Such methods utilise ligase enzymes such as DNA ligase to effect or catalyse the joining of the ends of the two polynucleotide strands, in this case, the single stranded template polynucleotide molecule and the primer oligonucleotide ligate such that covalent linkages are formed. In this context 'joining' means covalent linkage of two polynucleotide strands that were not previously covalently linked. Thus, an aim of certain embodiments of the invention can also be achieved by modifying the 3' end of a subset of primer oligonucleotides such that they are unable to ligate to the single stranded template polynucleotides. By way of non-limiting example, the addition of 2'3'dideoxy AMP (dideoxyAMP) by the enzyme terminal deoxynucleotidyl transferase (TdT) effectively prevents T4 DNA ligase from ligating treated molecules together.

An alternative method would be to have the capture oligonucleotides as duplex strands and the amplification oligonucleotides as single strands. Upon ligation of the single strands to the capture duplexes (which would be the only immobilised species carrying a free 5' phosphate) the 3' end of the immobilised strand can be extended as described above. Upon denaturation of the hybridised template sequence, amplification of the immobilised strand can proceed as described. Other such methods for attaching single strands will be apparent to those skilled in the art.

In a next step according to particular embodiments of the present invention, suitable conditions are applied to the immobilised single stranded polynucleotide molecule and the plurality of amplification oligonucleotides such that the single stranded polynucleotide molecule hybridises to an amplification oligonucleotide to form a complex in the form of a bridge structure. Suitable conditions such as neutralising and/or hybridising buffers are well known in the art (See Sambrook et al., supra; Ausubel et al., Current Protocols in Molecular Biology, John Wiley and Sons, Baltimore, Md. (1998)). The neutralising and/or hybridising buffer may then be removed.

Next by applying suitable conditions for extension an extension reaction is performed. The amplification oligonucleotide of the complex is extended by sequential addition of nucleotides to generate an extension product complementary to the single stranded polynucleotide molecule. The resulting duplex is immobilised at both 5' ends such that each strand is immobilised.

Suitable conditions such as extension buffers/solutions comprising an enzyme with polymerase activity are well known in the art (See Sambrook et al., supra; Ausubel et al. supra). In a particular embodiment dNTP's may be included in the extension buffer. In a further embodiment dNTP's could be added prior to the extension buffer. This bridge amplification technique can be carried out as described, for example, in U.S. Pat. No. 7,115,400 and US 2005/0100900 A1, the contents of which are incorporated herein by reference.

Examples of enzymes with polymerase activity which can be used in the present invention are DNA polymerase (Klenow fragment, T4 DNA polymerase), heat-stable DNA polymerases from a variety of thermostable bacteria (such as Taq, VENT, Pfu, or Tfl DNA polymerases) as well as their genetically modified derivatives (TaqGold, VENTexo, or Pfu exo). A combination of RNA polymerase and reverse transcriptase can also be used to generate the extension products. Particularly the enzyme may in these and related embodiments have strand displacement activity, more particularly the enzyme may be active at a pH of about 7 to about 9, particularly pH 7.9 to pH 8.8, yet more particularly the enzymes are in certain exemplary embodiments Bst or Klenow.

The nucleoside triphosphate molecules used are typically deoxyribonucleotide triphosphates, for example dATP, dTTP, dCTP, dGTP, or are ribonucleoside triphosphates for example ATP, UTP, CTP, GTP. The nucleoside triphosphate molecules may be naturally or non-naturally occurring.

After the hybridisation and extension steps, the support and attached nucleic acids can be subjected to denaturation conditions. A flow cell can be used such that, the extension buffer is generally removed by the influx of the denaturing buffer. Suitable denaturing buffers are well known in the art (See Sambrook et al., supra; Ausubel et al. supra). By way of example it is known that alterations in pH and low ionic strength solutions can denature nucleic acids at substantially isothermal temperatures. Formamide and urea form new hydrogen bonds with the bases of nucleic acids disrupting hydrogen bonds that lead to Watson-Crick base pairing. In a particular embodiment the concentration of formamide is 50% or more. These result in single stranded nucleic acid molecules. If desired, the strands may be separated by treatment with a solution of very low salt (for example less than 0.01 M cationic conditions) and high pH (>12) or by using a chaotropic salt (e.g. guanidinium hydrochloride). In a particular embodiment a strong base is used. A strong base is a basic chemical compound that is able to deprotonate very weak acids in an acid base reaction. The strength of a base is indicated by its pKb value, compounds with a pKb value of less than about 1 are called strong bases and are well known to one skilled in the art. In a particular embodiment the strong base is Sodium Hydroxide (NaOH) solution used at a concentration of from 0.05 M to 0.25 M, particularly 0.1 M.

Following the hybridization, extension and denaturation steps exemplified above, two immobilised nucleic acids will be present, the first containing a sequence the same as the first template single stranded polynucleotide molecule (that was initially immobilised) and the second being a nucleic acid complementary thereto, extending from one of the immobilised capture oligonucleotides. Both the immobilised strands are then able to initiate further rounds of amplification by subjecting the support to further cycles of hybridisation, extension and denaturation. Thus the amplification proceeds from a single strand to a duplex, one duplex to two duplexes, two duplexes to four duplexes etc. throughout the cycles of annealing, extension and denaturation.

It may be advantageous to perform optional washing steps in between each step of the amplification method. For example an extension buffer without polymerase enzyme with or without dNTPs could be applied to the solid support before being removed and replaced with the full extension buffer.

Such further rounds of amplification can be used to produce a nucleic acid colony or 'cluster' comprising multiple immobilised copies of the single stranded polynucleotide sequence and its complementary sequence.

The initial immobilisation of the template polynucleotide molecule means that the extension product can hybridise with amplification oligonucleotides located at a distance within the total length of the template polynucleotide molecule. Other surface bound primers that are out of reach will not hybridize to the extension product. Thus the boundary of the nucleic acid colony or cluster formed is limited to a relatively local area surrounding the location in which the initial template polynucleotide molecule was immobilised.

Once more copies of the polynucleotide extension products molecule and its complement have been synthesised by carrying out further rounds of amplification, i.e. further rounds of hybridisation, extension and denaturation, then the boundary of the nucleic acid colony or cluster being generated will be able to be extended further, although the boundary of the colony formed is still limited to a relatively local area around the location in which the initial single stranded polynucleotide molecule was immobilised. For example the size of each amplified cluster may be 0.5-5 microns, and can be controlled by the number of cycles performed.

It can thus be seen that the method of the present invention allows the generation of a plurality of nucleic acid colonies from multiple single immobilised single stranded polynucleotide molecules and that the density of these colonies can be controlled by altering the proportions of modified capture/amplification oligonucleotides used to graft the surface of the solid support.

In one embodiment, the hybridisation, extension and denaturation steps are all carried out at the same, substantially isothermal temperature. For example the temperature is from 37° ° C. to about 75° C., particularly from 50° ° C. to 70° C., yet more particularly from 60° C. to 65° C. In a particular embodiment the substantially isothermal temperature may be the optimal temperature for the desired polymerase.

In a particular aspect, the method according to the first aspect of the invention is used to prepare clustered arrays of nucleic acid colonies, analogous to those described in U.S. Pat. No. 7,115,400, US 2005/0100900 A1, WO 00/18957 and WO 98/44151 (the contents of which are herein incorporated by reference), by solid-phase amplification.

In yet another aspect more than one capture oligonucleotides and more than two amplification oligonucleotides, for example, at least three or four or more, different amplification oligonucleotide sequences may be grafted to the solid support. In this manner more than one library, with common sequences which differ between the libraries, could be utilised to prepare clusters, such as, for example libraries prepared from two different patients. Alternatively different selected regions could be amplified simultaneously by using different amplification oligonucleotides. Whilst the clusters may overlap in space, they would be able to be sequenced one after the other due to the differences between the ends of the templates. For example, two different samples can be captured using two different capture oligonucleotides. These can be amplified from the same two amplification oligonucleotides. The samples can be differentiated due to the two different capture oligonucleotides, which can be used as the sites for hybridisation of two different sequencing primers. The use of different capture oligonucleotides thereby gives rise to a method of sample indexing using different sequencing primers.

Clustered arrays formed by the methods of the invention are suitable for use in applications usually carried out on ordered arrays such as micro-arrays. Such applications by way of non-limiting example include hybridisation analysis, gene expression analysis, protein binding analysis, sequencing, genotyping, nucleic acid methylation analysis and the like. The clustered array may be sequenced before being used for downstream applications such as, for example, hybridisation with fluorescent RNA or binding studies using fluorescent labelled proteins.

Sequencing Methods

The invention also encompasses methods of sequencing amplified nucleic acids generated by solid-phase amplification. Thus, the invention provides a method of nucleic acid sequencing comprising amplifying a pool of nucleic acid templates using solid-phase amplification as described above and carrying out a nucleic acid sequencing reaction to determine the sequence of the whole or a part of at least one amplified nucleic acid strand produced in the solid-phase amplification reaction.

Sequencing can be carried out using any suitable sequencing technique. A particularly useful method is one wherein nucleotides are added successively to a free 3' hydroxyl group, resulting in synthesis of a polynucleotide chain in the 5' to 3' direction. The nature of the nucleotide added may be determined after each nucleotide addition or at the end of the sequencing process. Sequencing techniques using sequencing by ligation, wherein not every contiguous base is sequenced, and techniques such as massively parallel signature sequencing (MPSS) where bases are removed from, rather than added to the strands on the surface are also within the scope of the invention.

The initiation point for the sequencing reaction may be provided by annealing of a sequencing primer to a product of the solid-phase amplification reaction. In this connection, one or both of the adaptors added during formation of the template library may include a nucleotide sequence which permits annealing of a sequencing primer to amplified products derived by whole genome or solid-phase amplification of the template library.

The products of solid-phase amplification reactions wherein both forward and reverse amplification oligonucleotides are covalently immobilised on the solid surface are so-called 'bridged' structures formed by annealing of pairs of immobilised polynucleotide strands and immobilised complementary strands, both strands being attached to the solid support at the 5' end. Arrays comprised of such bridged structures provide inefficient templates for typical nucleic acid sequencing techniques, since hybridisation of a conventional sequencing primer to one of the immobilised strands is not favoured compared to annealing of this strand to its immobilised complementary strand under standard conditions for hybridisation.

In order to provide more suitable templates for nucleic acid sequencing, it may be advantageous to remove or displace substantially all or at least a portion of one of the immobilised strands in the 'bridged' structure in order to generate a template which is at least partially single-stranded. The portion of the template which is single-stranded will thus be available for hybridisation to a sequencing primer. The process of removing all or a portion of one immobilised strand in a 'bridged' double-stranded nucleic acid structure may be referred to herein as linearization', and is described in further detail in WO07010251 and US20090118128, the contents of which are incorporated herein by reference in their entirety.

Bridged template structures may be linearized by cleavage of one or both strands with a restriction endonuclease or by cleavage of one strand with a nicking endonuclease. Other methods of cleavage can be used as an alternative to restriction enzymes or nicking enzymes, including inter alia chemical cleavage (e.g., cleavage of a diol linkage with periodate), cleavage of abasic sites by cleavage with endonuclease (for example 'USER', as supplied by NEB, Ipswich, MA, USA, part number M5505S), or by exposure to heat or alkali, cleavage of ribonucleotides incorporated into amplification products otherwise comprised of deoxyribonucleotides, photochemical cleavage or cleavage of a peptide linker.

Following the cleavage step, regardless of the method used for cleavage, the product of the cleavage reaction may be subjected to denaturing conditions in order to remove the portion (s) of the cleaved strand (s) that are not attached to the solid support. Suitable denaturing conditions, for example sodium hydroxide solution, formamide solution or heat, will be apparent to the skilled reader with reference to standard molecular biology protocols (Sambrook et al., supra; Ausubel et al. supra). Denaturation results in the production of a sequencing template which is partially or substantially single-stranded. A sequencing reaction may then be initiated by hybridisation of a sequencing primer to the single-stranded portion of the template.

Thus, the invention encompasses methods wherein the nucleic acid sequencing reaction comprises hybridising a sequencing primer to a single-stranded region of a linearized amplification product, sequentially incorporating one or more nucleotides into a polynucleotide strand complementary to the region of amplified template strand to be sequenced, identifying the base present in one or more of the incorporated nucleotide (s) and thereby determining the sequence of a region of the template strand.

One sequencing method which can be used in accordance with the invention relies on the use of modified nucleotides having removable 3' blocks, for example as described in WO04018497, US 2007/0166705A1 and U.S. Pat. No. 7,057,026, the contents of which are incorporated herein by reference in their entirety. Once the modified nucleotide has been incorporated into the growing polynucleotide chain complementary to the region of the template being sequenced there is no free 3'-OH group available to direct further sequence extension and therefore the polymerase can not add further nucleotides. Once the nature of the base incorporated into the growing chain has been determined, the 3' block may be removed to allow addition of the next successive nucleotide. By ordering the products derived using these modified nucleotides, it is possible to deduce the DNA sequence of the DNA template. Such reactions can be done in a single experiment if each of the modified nucleotides has a different label attached thereto, known to correspond to the particular base, to facilitate discrimination between the bases added during each incorporation step. Alternatively, a separate reaction may be carried out containing each of the modified nucleotides separately.

The modified nucleotides may carry a label to facilitate their detection. A fluorescent label, for example, may be used for detection of modified nucleotides. Each nucleotide type may thus carry a different fluorescent label, for example, as described in US Provisional Application No. 60/801,270 (Novel dyes and the use of their labelled conjugates), published as WO07135368, the contents of which are incorporated herein by reference in their entirety. The detectable label need not, however, be a fluorescent label. Any label can be used which allows the detection of an incorporated nucleotide.

One method for detecting fluorescently labelled nucleotides comprises using laser light of a wavelength specific for the labelled nucleotides, or the use of other suitable sources of illumination. The fluorescence from the label on the nucleotide may be detected by a CCD camera or other suitable detection means. Suitable instrumentation for recording images of clustered arrays is described in U.S. Provisional Application No. 60/788,248 (Systems and devices for sequence by synthesis analysis), published as WO07123744, the contents of which are incorporated herein by reference in their entirety. The invention is not intended to be limited to use of the sequencing method outlined above, as essentially any sequencing methodology which relies on successive incorporation of nucleotides into a polynucleotide chain can be used. Suitable alternative techniques include, for example, Pyrosequencing™, FISSEQ (fluorescent in situ sequencing), MPSS and sequencing by ligation-based methods, for example as described in U.S. Pat. No. 6,306,597 which is incorporated herein by reference.

The nucleic acid sample may be further analysed to obtain a second read from the opposite end of the fragment. Methodology for sequencing both ends of a cluster are described in co-pending applications WO07010252, PCTGB2007/003798 and US 20090088327, the contents of which are incorporated by reference herein in their entirety. In one example, the series of steps may be performed as follows; generate clusters, linearize, hybridise first sequencing primer and obtain first sequencing read. The first sequencing primer can be removed, and in the cases where a tag sequence is present in the cluster, a second primer hybridised and the tag sequenced. The nucleic acid strand may then be 'inverted' on the surface by synthesising a complementary copy from the remaining immobilised primers used in cluster amplification. This process of strand resynthesis regenerates the double stranded cluster. The original template strand can be removed, to linearize the resynthesized strand that can then be annealed to a sequencing primer and sequenced in a second or third sequencing run.

In the cases where strand resynthesis is employed, both strands can be immobilised to the surface in a way that allows subsequent release of a portion of the immobilised strand. This can be achieved through a number of mechanisms as described in WO07010251 and US20090118128, the contents of which are incorporated herein by reference in their entirety. For example, one primer can contain a uracil nucleotide, which means that the strand can be cleaved at the uracil base using the enzymes uracil glycosylase (UDG) which removes the nucleoside base, and endonuclease VIII that excises the abasic nucleotide. This enzyme combination is available as USER™ from New England Biolabs (NEB, Ipswich, MA, USA, part number M5505). The second primer may comprise an 8-oxoguanine nucleotide, which is then cleavable by the enzyme FPG (NEB part number M0240). This design of primers gives control of which primer is cleaved at which point in the process, and also where in the cluster the cleavage occurs. The primers may also be chemically modified, for example with a disulfide or diol modification that allows chemical cleavage at specific locations.

Flow Cells

The invention also relates to flow cells for the preparation of amplified arrays of nucleic acids wherein the flow cells contain a uniform coating of three, four or more immobilised primers. Thus a substrate described herein can occur within or as a part of a flow cell and the methods set forth herein can be carried out in a flow cell. In contrast to spotted arrays of multiple sequences, the three, four or more oligonucleotides can be coated over the whole of the array surface rather than in discreet locations that comprise different sequences in each small location. The arrays may be of a size of 1 cm² or greater whereby the whole 1 cm² or greater comprises a homogeneous coating of multiple copies of the same three, four or more sequences. A flow cell can be distinguished from a 'spotted array' or photolithographically synthesised array due to the fact that the oligonucleotides are attached to each and every surface; top, bottom, walls and ends of the flow cell chamber, rather than being an array that is mounted in a housing. However, if desired a flow cell that is used in a method set forth herein can have surfaces with different reactivity for oligonucleotides such that the oligonucleotides are only attached to one or a subset of the aforementioned surfaces or even to only a subset of regions within these surfaces.

The flow cell may in certain embodiments be coated with three oligonucleotide species of different sequence composition, namely two amplification oligonucleotides and a capture oligonucleotide. The flow cell may in certain embodiments be coated with no more than the three oligonucleotide species. However in other particular embodiments, the flow cell can further include one or more other oligonucleotide species whether an amplification oligonucleotide, capture oligonucleotide, or other species of oligonucleotide. The capture oligonucleotide may be present at a lower concentration than the amplification oligonucleotide, for example at least 100, 1000 or 100,000 fold lower relative concentration. The two amplification oligonucleotides may be present at similar ratios to each other, for example varying by less than a factor of two. The capture oligonucleotides may be longer than the amplification oligonucleotides, and may comprise the amplification oligonucleotide sequence region plus a capture oligonucleotide region, as shown for example in FIG. 1. Alternatively or additionally, the amplification oligonucleotides may be blocked to prevent hybridisation and/or extension. The sequence of the capture oligonucleotides may be different between different capture oligonucleotides. In certain related but distinct embodiments the flow cell may be coated with at least four species of oligonucleotides having different sequences, wherein at least a first and a second of the four species are present at a lower density than the third and fourth of the four species. For example, the first and second species may be capture oligonucleotides and the third and fourth species may be amplification oligonucleotides. Thus, in the above described embodiments and in other related embodiments that are contemplated, a solid support may carry two or more capture oligonucleotides of different sequences. The sequence of the capture oligonucleotides can allow for selection of a known portion of the nucleic acid sample. The capture sequences may be produced by extending some or all of the amplification sequences.

Although the invention has been exemplified herein for embodiments using nucleic acid species, it will be understood that the same principles can be applied to other molecular species. For example, surfaces of substrates can be derivatized with other synthetic molecules such as peptides, small molecule ligands, saccharides or the like. By controlling the amount of different species of such molecules in the derivatization step, a desired density of each species can result. Samples of molecules that bind to one or more of these solid phase molecules can be used without the need for titrating the samples because the density of molecules from the sample that bind to the surfaces will be controlled by the density of their binding partners on the surface. Accordingly, attachment of molecules from the sample can be controlled thermodynamically in a process that is allowed to proceed to equilibrium as opposed to a kinetic process that requires more precise control of reaction conditions and incubation times. Once bound to the surface the molecules from the sample can be subsequently modified or detected. In such embodiments, the surface can include reversibly modified synthetic molecules such that altering or removing the modification can allow the molecules from the sample to be modified or detected for a particular analytical assay or step.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

What is claimed is:

1. A method of controlling for different amounts of template nucleic acids in different samples in solid phase amplification reactions, comprising:
   (a) obtaining a first flow cell comprising a plurality of oligonucleotides immobilized on the first flow cell, wherein the plurality of oligonucleotides comprises a plurality of capture probes and a plurality of amplification primers, wherein the capture probes are immobilized on the first flow cell at a density lower than the amplification primers;
   (b) selectively hybridizing first template nucleic acids to the capture probes, wherein the first template nucleic acids have a concentration sufficient to selectively hybridize to all of the capture probes on the first flow cell;
   (c) extending the capture probes hybridized to the first template nucleic acids to obtain extended polynucleotides;
   (d) removing the first template nucleic acids from the extended polynucleotides;
   (e) amplifying the extended polynucleotides by hybridizing the extended polynucleotides to the amplification primers to obtain amplified first template nucleic acids; and
   (f) repeating steps (a)-(e) with a second flow cell and second template nucleic acids,
      wherein a density of the capture probes on the first flow cell is the same as a density of the capture probes on the second flow cell, and wherein a density of the amplified first template nucleic acids on the first flow cell is the same as a density of the amplified second template nucleic acids on the second flow cell.

2. The method of claim 1, wherein the amplification primers are blocked prior to step (d); and wherein step (d) further comprises deblocking the amplification primers.

3. The method of claim 2, wherein the amplification primers are blocked from extension by a chemical species attached to a 3' end of the amplification primers.

4. The method of claim 3, wherein the chemical species is a phosphate group.

5. The method of claim 1, wherein the amplifying comprises bridge amplification.

6. The method of claim 1, wherein the amplifying comprises isothermal amplification.

7. The method of claim 1, wherein the capture probes are immobilised on the first flow cell at a density of at least 2-fold lower than the amplification primers.

8. The method of claim 7, wherein the capture probes are immobilised on the first flow cell at a density of at least 100-fold lower than the amplification primers.

9. The method of claim 1, wherein the capture probes are longer than the amplification primers.

10. The method of claim 9, wherein capture probes comprise the sequence of the amplification primers.

11. The method of claim 1, wherein the first template nucleic acids are different from one another.

12. The method of claim 1, wherein at least one end of the first and second template nucleic acids comprises an adapter sequence.

13. The method of claim 12, wherein the first template nucleic acids comprise the same adapter sequences.

14. The method of claim 12, wherein the amplification primers comprise a nucleotide sequence capable of hybridizing to the adapter sequence or a complement thereof.

15. The method of claim 1 wherein the first template nucleic acids are obtained from a population of organisms.

16. The method of claim 1, wherein the first template nucleic acids comprise genomic DNA.

17. The method of claim 1, further comprising obtaining the first template nucleic acids by ligating adapters to ends of a plurality of nucleic acid fragments.

18. The method of claim 1, further comprising sequencing the amplified first template nucleic acids.

19. A method of controlling for different amounts of template nucleic acids in different samples in solid phase amplification reactions, comprising:
   (a) performing a first selective amplification on a first flow cell with first template nucleic acids to obtain amplified first template nucleic acids, comprising:
      (i) obtaining the first flow cell comprising a first plurality of oligonucleotides immobilized thereon, wherein the first plurality of oligonucleotides comprises a plurality of first capture probes and a plurality of first amplification primers, wherein the first capture probes are immobilized on the first flow cell at a density lower than the first amplification primers,
      (ii) selectively hybridizing the first template nucleic acids to the first capture probes, wherein the first template nucleic acids have a concentration sufficient to selectively hybridize to all of the capture probes on the first flow cell,
      (iii) extending the first capture probes hybridized to the first template nucleic acids to obtain first extended polynucleotides, and
      (iv) removing the first template nucleic acids from the first extended polynucleotides, and
      (v) amplifying the first extended polynucleotides by hybridizing the first extended polynucleotides to the first amplification primers to obtain the amplified first template nucleic acids; and
   (b) performing a second selective amplification on a second flow cell with second template nucleic acids to obtain amplified second template nucleic acids, comprising;
      (i) obtaining the second flow cell comprising a second plurality of oligonucleotides immobilized thereon, wherein the second plurality of oligonucleotides comprises a plurality of second capture probes and a plurality of second amplification primers, wherein the second capture probes are immobilized on the second flow cell at a density lower than the second amplification primers, and wherein a density of the second capture probes immobilized on the second flow cell is the same as a density of the first capture probes immobilized on the first flow cell,
      (ii) selectively hybridizing the second template nucleic acids to the second capture probes, wherein the second template nucleic acids have a concentration sufficient to selectively hybridize to all of the capture probes on the second flow cell,
      (iii) extending the second capture probes hybridized to the second template nucleic acids to obtain second extended polynucleotides,
      (iv) removing the second template nucleic acids from the second extended polynucleotides, and
      (v) amplifying the second extended polynucleotides by hybridizing the second extended polynucleotides to the second amplification primers to obtain the amplified second template nucleic acids;

wherein a density of the amplified first template nucleic acids on the first flow cell is the same as a density of the amplified second template nucleic acids on the second flow cell.

20. The method of claim 19, wherein the first and second amplification primers are blocked prior to the extending steps; and wherein the first and second amplification primers are deblocked prior to the amplifying steps.

21. The method of claim 1, wherein the density of the capture probes on the first flow cell is such that amplifying the extended polynucleotides provides a cluster density of the amplified first template nucleic acids in a range from $10^6$ to $10^9$ clusters per cm$^2$.

22. The method of claim 1, wherein a ratio of the capture probes on the first flow cell to the amplification primers on the first flow cell is the same as a ratio of the capture probes on the second flow cell to the amplification primers on the second flow cell.

23. The method of claim 22, wherein the ratio of the capture probes on the first flow cell to the amplification primers on the first flow cell is at least 1:100.

\* \* \* \* \*